United States Patent
Hermann Fakler et al.

(10) Patent No.: US 11,744,633 B2
(45) Date of Patent: Sep. 5, 2023

(54) CONNECTOR PLUG FOR A MEDICAL INSTRUMENT

(71) Applicant: Sutter Medizintechnik GmbH, Freiburg (DE)

(72) Inventors: Michael Otto Hermann Fakler, Freiburg (DE); Dirk Weitkamp, Waldkirch (DE)

(73) Assignee: Sutter Medizintechnik GmbH, Emmendingen (DE)

( * ) Notice: Subject to any disclaimer, the term of this patent is extended or adjusted under 35 U.S.C. 154(b) by 918 days.

(21) Appl. No.: 15/809,094

(22) Filed: Nov. 10, 2017

(65) Prior Publication Data
US 2018/0132924 A1 May 17, 2018

(30) Foreign Application Priority Data
Nov. 11, 2016 (DE) .................. 10 2016 121 701.8

(51) Int. Cl.
| | |
|---|---|
| A61B 18/12 | (2006.01) |
| A61B 18/14 | (2006.01) |
| H01R 43/20 | (2006.01) |
| H01R 11/18 | (2006.01) |
| H01R 4/48 | (2006.01) |
| A61B 18/00 | (2006.01) |
| H01R 4/02 | (2006.01) |

(Continued)

(52) U.S. Cl.
CPC ........... *A61B 18/1442* (2013.01); *H01R 4/48* (2013.01); *H01R 11/18* (2013.01); *H01R 43/20* (2013.01); *A61B 2018/00083* (2013.01); *A61B 2018/00172* (2013.01); *A61B 2018/00178* (2013.01); *A61B 2018/126* (2013.01); *A61B 2018/1462* (2013.01); *H01R 4/023* (2013.01); *H01R 24/66* (2013.01); *H01R 2103/00* (2013.01); *H01R 2201/12* (2013.01)

(58) Field of Classification Search
CPC ...... A61B 18/1442; A61B 2018/00172; A61B 2018/00083; A61B 2018/126; A61B 2018/1462; A61B 2018/00178; H01R 43/20; H01R 11/18; H01R 4/48; H01R 24/66; H01R 2103/00; H01R 2201/12; H01R 4/023
See application file for complete search history.

(56) References Cited

U.S. PATENT DOCUMENTS

| | | | | |
|---|---|---|---|---|
| 4,819,633 A | * | 4/1989 | Bauer ................ | A61B 18/1442 |
| | | | | 606/52 |
| 5,334,215 A | * | 8/1994 | Chen ..................... | A61B 17/30 |
| | | | | 294/99.2 |

(Continued)

FOREIGN PATENT DOCUMENTS

DE 199 34 532 A1 4/2001

*Primary Examiner* — Khadijeh A Vahdat
*Assistant Examiner* — Yasamin Ekrami
(74) *Attorney, Agent, or Firm* — Budzyn IP Law, LLC (57) ABSTRACT

The invention relates to a connector plug for a medical instrument, in particular a bipolar electrode or forceps, comprising an insulating body for connecting two limbs of the instrument, wherein the insulating body has openings for receiving, inserting or sliding in the limbs, wherein in each of the openings a latching or spring element is provided for fastening one of the limbs of the instrument in the insulating body.

18 Claims, 5 Drawing Sheets

(51) Int. Cl.
*H01R 24/66* (2011.01)
*H01R 103/00* (2006.01)

(56) References Cited

U.S. PATENT DOCUMENTS

| | | | | |
|---|---|---|---|---|
| 5,632,652 | A * | 5/1997 | Zell | H01R 13/6585 |
| | | | | 439/581 |
| 5,891,142 | A * | 4/1999 | Eggers | A61B 18/1442 |
| | | | | 606/51 |
| 6,343,961 | B1 | 2/2002 | Sutter | |
| 6,749,610 | B2 * | 6/2004 | Kirwan, Jr. | A61B 18/1442 |
| | | | | 29/825 |
| 2004/0097912 | A1 * | 5/2004 | Gonnering | H01R 27/02 |
| | | | | 606/34 |
| 2007/0032789 | A1 * | 2/2007 | Gonnering | A61B 18/14 |
| | | | | 606/49 |
| 2009/0012519 | A1 * | 1/2009 | Manrique | A61B 18/1442 |
| | | | | 606/51 |
| 2014/0200576 | A1 * | 7/2014 | Scheller | A61B 18/1445 |
| | | | | 606/41 |
| 2014/0235085 | A1 * | 8/2014 | Su | H01R 13/6277 |
| | | | | 439/346 |
| 2017/0196578 | A1 * | 7/2017 | Zubrod | B33Y 10/00 |
| 2018/0055558 | A1 * | 3/2018 | Cornacchia | A61B 18/1442 |

\* cited by examiner

CONNECTOR PLUG FOR A MEDICAL INSTRUMENT

FIELD OF THE INVENTION

The invention relates to a connector plug for a medical instrument, in particular a bipolar electrode or forceps, comprising an insulating body for connecting two limbs of the instrument, wherein the insulating body has openings for receiving, inserting or sliding in the limbs.

BACKGROUND

One such connector plug is known from DE 199 34 532. Similar connector plugs enable the modular final assembly of medical devices. The two forceps limbs can be connected to one another by means of an insulating body at their proximal end with the connector plug. According to DE 199 34 532, the insulating body is provided for feeding through the forceps limbs and fastening them by means of a ring-shaped locking part. In this case, the limbs form the connections for a current source at the proximal end of the insulating body.

A connector plug of this type has the disadvantage that the final assembly must be carried out in several, sometimes complex, working steps. Moreover, manufacturing tolerances on the forceps limbs can not be readily compensated.

It is an object of the present invention to provide a connector plug of the type described above which can compensate for manufacturing inaccuracies in the limbs of the medical instrument and permit a final assembly of the medical instrument in as few, simple working steps as possible.

BRIEF DESCRIPTION OF THE INVENTION

This object is achieved by the invention specified in the independent claims. Advantageous further developments can be found in the subclaims.

In order to achieve the described object, it is provided according to the invention that a latching or spring element is provided in each of the openings for fastening one of the limbs of the instrument in the insulating body.

The connector plug according to the invention makes it possible to stick the components of the medical instrument together in a simple manner. For this purpose, the limbs of the instrument are inserted into the latching or spring element and fastened to the insulating body by latching and/or form-locking. Subsequently, the openings of the insulating body with the limbs accommodated therein can be filled with an epoxy resin and sealed. After the epoxy resin has cured, the two limbs of the instrument are connected to each other non-detachably.

A further advantage of the latching or spring elements is the compensation of production tolerances of the limbs. Due to the manufacturing process, the limbs can have tolerances which make the final assembly of the medical instrument more difficult. The latching or spring elements adapt themselves to the limbs of the instrument and fix them despite the tolerances in the connector plug. As a result, the production process of the limbs can also be made less complex.

In one embodiment of the invention, the latching or spring elements each have a substantially U-shaped cross-section, wherein one limb of the instrument is insertable and/or latchable into the latching or spring element via the open side of the cross-section. In particular, the latching or spring elements each have two fastening limbs, which run substantially parallel to one another at least in sections, wherein at least one of the fastening limbs is configured elastic and movable relative to the other fastening limb so that one limb of the instrument is clampable between the fastening limbs of the latching or spring elements. This form of the latching or spring elements permits a particularly simple and at the same time stable mounting of the limbs of the instrument.

In one embodiment, at least one of the fastening limbs, in particular the elastically configured fastening limbs, has an inwardly pointing nose-like projection. The nose-like projection can be used to engage and latch a cavity or depression on the forceps limb. As a result, the forceps limb is stably fastened in the connector plug.

In one embodiment of the invention, the other fastening limb has a planar inner side lying opposite the projection. The inner side forms a planar contact surface for the limbs so that a good electrical connection is established between the limbs and the latching or spring element.

In one embodiment of the invention, the insulating body is formed by a plastic sleeve made of insulating material, the plastic sleeve being rotationally symmetrical, in particular cylindrical and/or to a longitudinal axis. The sleeve is one-piece and cost-effective, producible in any form as a mass part.

In an embodiment of the invention, the openings each have, viewed in the cross-section perpendicular to a longitudinal axis of the insulating body, two opposing, planar and non-parallel side walls, between which one end of a limb of the instrument is clampable. The surfaces enable the limbs to be fixed and aligned. They create a positive and therefore mechanically stable connection between the limbs and the inner walls of the connector plug. They also make it possible to compensate for production tolerances in the thickness and/or width of the limbs.

In one embodiment of the invention, the insulating body has one or more inlet channels for filling the insulating body with a casting compound, in particular an epoxy resin, wherein the inlet channel or channels, in particular, is/are arranged together with the openings (4) on one end face of the insulating body (11). The cavity in the insulating body can be filled with a casting compound through the inlet channels without bubbles.

According to the invention, there is also provided a medical instrument comprising two limbs, in particular electrode shafts, and a connector plug as described above, wherein the ends of the limbs of the instrument are received in the insulating body of the connector plug and are fastened therein.

Preferably, the outer sides of the limbs are configured at least partially complementary to the inner sides of the latching or spring element so that the limbs are at least partially positively connected to the latching or spring elements. In particular, in the case of both limbs, viewed in the cross-section, a projection is configured at the one end, which projection is engaged behind through the nose-like projection on the inner side of the latching or spring elements and/or a depression in which the nose-like projection comes to rest. In this way, the limbs are fixable against tensile stress in the latching or spring elements and secured against unintentional slipping during the manufacturing process.

In one embodiment, the limbs of the instrument form electrodes, wherein the fastening limbs of the connector plug are made of electrically conductive material and create an electrical connection to the electrodes.

In a further embodiment, the medical instrument has two contact pins which penetrate the insulating body on a proximal end face and which are electrically connected on the one hand to the latching or spring elements, and on the other hand, provide a connection of the instrument to an external current source.

In one embodiment, the contact pins are formed by metal bodies which are configured plate-shaped or platelet-shaped and in particular form a flat plug. In other words, the contact pins have an elongated, flat shape and allow connection to existing current sources with corresponding, where necessary standardized, connections.

In one embodiment, the instrument comprises, instead of the contact pins, two cables having electrical leads contained therein, wherein the cables penetrate the insulating body at a proximal end face, and wherein the electrical leads on the one hand are electrically connected to the latching or spring elements, and on the other hand provide a connection to an external current source. In this embodiment, the connection point is not exposed and thus protected against contamination. This embodiment is particularly suitable for instruments which are intended for single use.

In one embodiment of the medical instrument, the contact pins are welded or soldered to the latching or spring elements. This type of connection is particularly solid and has good electrical properties.

According to the invention, a method is also provided for producing a medical instrument, in particular a bipolar electrode or forceps, having a connector plug with the features described above, wherein the method comprising connecting the electrodes or forceps limbs with the connector plug by receiving, inserting or sliding in the proximal ends of the electrodes into the latching or spring elements of the connector plug, and creating a fixed, non-detachable connection between the electrodes and the connector plug.

In one embodiment, the non-detachable connection is produced by sealing the openings with casting compound, in particular epoxy resin.

In one embodiment of the method, the casting compound is introduced into the insulating body by one or more channels provided for it in the insulating body. This enables the filling of the insulating body with casting compound without bubbles.

BRIEF DESCRIPTION OF THE DRAWINGS

Exemplary embodiments of the invention are described in more detail below with reference to the accompanying drawings. They show.

FIGURE DESCRIPTION

Figure 1:
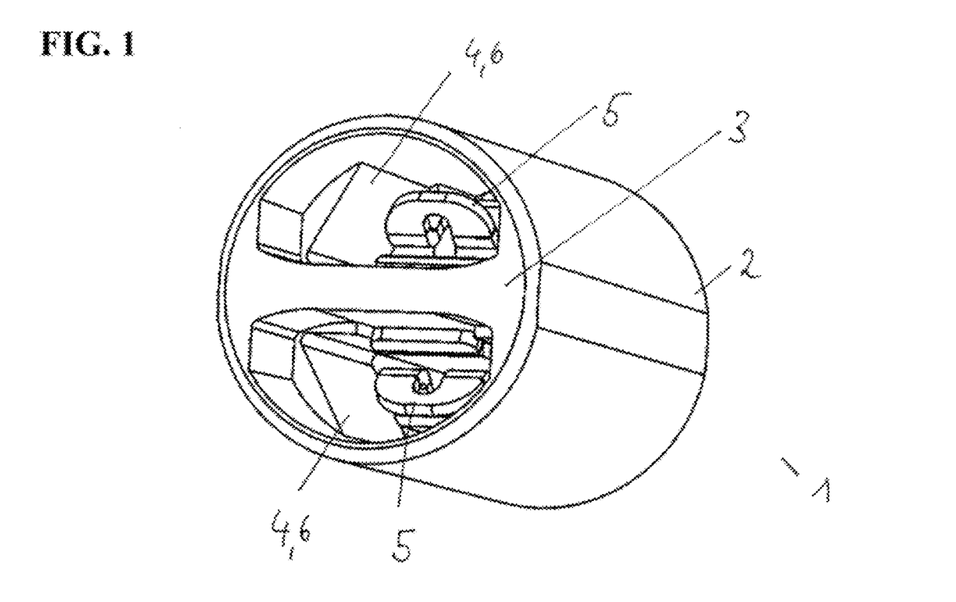
FIG. 1 is a perspective representation of an exemplary embodiment of a connector plug according to the invention.
Figure 2:
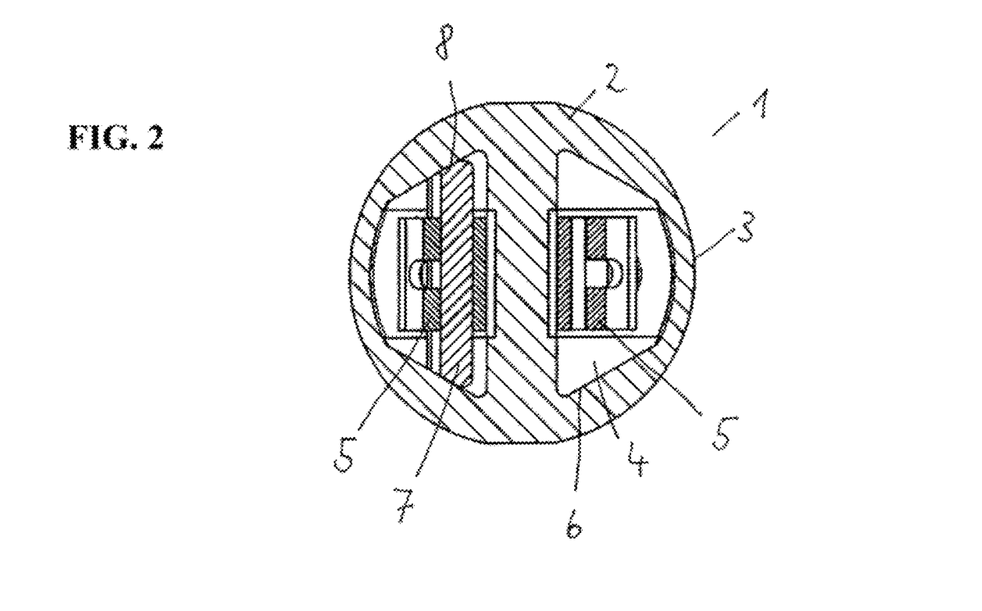
FIG. 2 is a sectional representation of an exemplary embodiment of the connector plug.

FIG. 1 shows an exemplary embodiment of the connector plug 1 in a perspective representation. The connector plug 1 comprises a cylindrical insulating body 2 which has openings 4 on one end face 3. The insulating body can also have any other shape. As can be seen clearly in FIGS. 2 and 3, the openings 4 have an approximately trapezoidal cross-section, wherein the limbs of the trapezoids are in each case formed by opposing planar and non-parallel inner walls 6.

A spring element 5 is arranged in each case in the interior of the openings 4. In the left opening 4 in FIG. 2, a limb of an instrument 7 is inserted into the spring element 5. The limb of the instrument 7 is loaded by the spring element 5 and fixed therein. The limb of the instrument 7 has beveled side walls 8 which project laterally beyond the spring element 5 and lie against the inner walls 6 of the insulating body 2.

Figure 3:
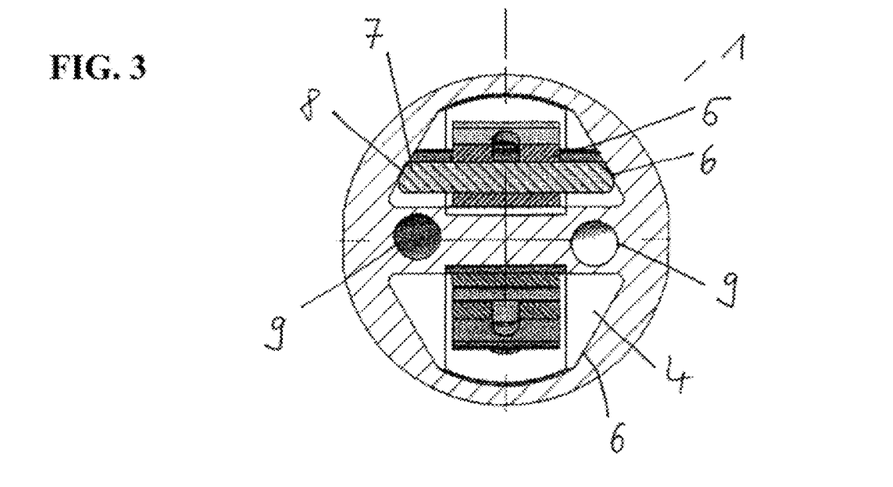
FIG. 3 is a further sectional representation of an exemplary embodiment of the connector plug.

As shown in FIG. 3, the insulating body 2 has channels 9 on the end face 3. The channels 9 extend from the end face 3 of the insulating body 2 into the interior of the insulating body 2. The channels 9 provide a connection between the end face 3 of the insulating body and the inner regions of the openings 4. The openings 4 can be filled with a casting compound, for example, epoxy resin, through the channels.

Figure 4:
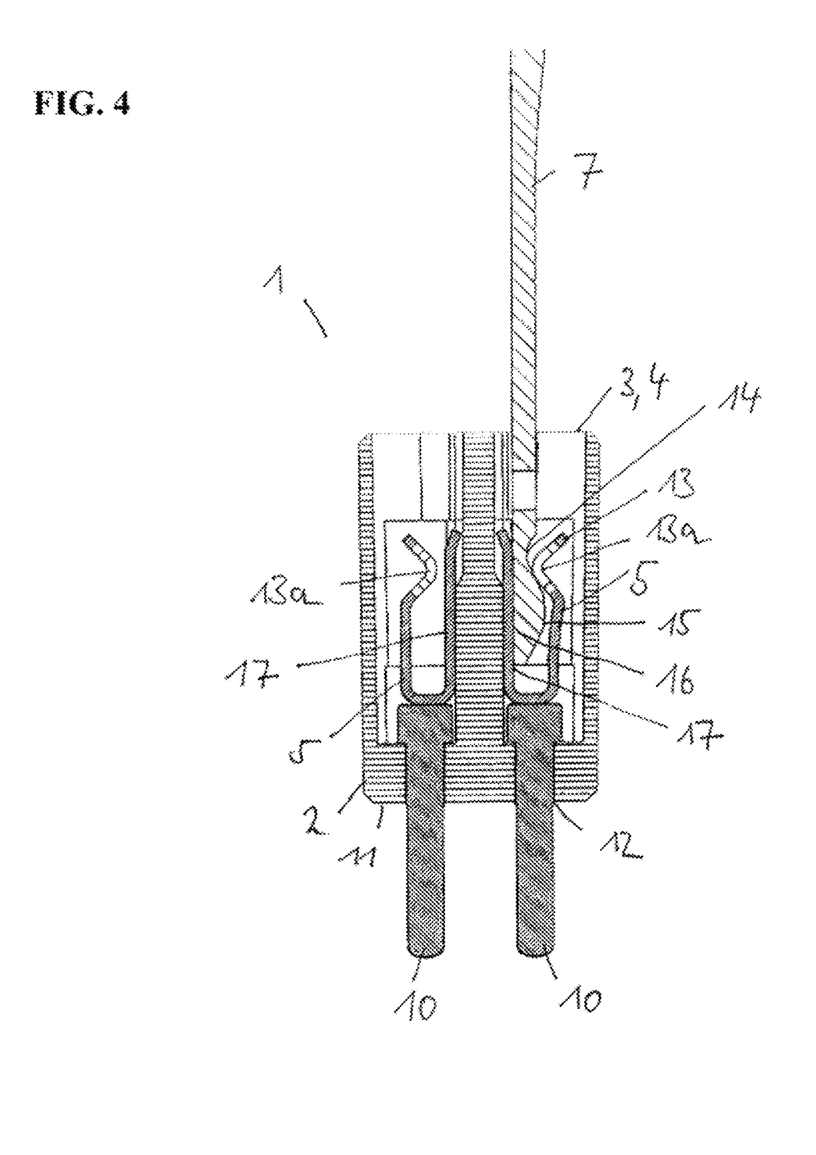
FIG. 4 is a sectional representation of an exemplary embodiment of the connector plug with a pushed-in electrode shaft.

FIG. 4 shows a cross-section of the connector plug 1 along the longitudinal axis of the insulating body 2. The spring elements 5 are each configured approximately U-shaped and are welded at one end to contact pins 10 which extend through passage openings 12 on a further end face 11 of the insulating body toward the outside. The contact pins 10 have a T-shaped cross-section. The contact pins 10 each have a head-like thickening at their end regions positioned within the insulating body 2. The contact pins 10 are introduced together with the spring elements 5 from the end face 3 of the insulating body 2 through the openings 4 into the insulating body 2 and are fixed with the head-like thickening against an edge of the passage openings 12 lying in the insulating body 2.

The spring elements 5 are designed as U-shaped clamp elements. Each of the spring elements 5 each has two fastening limbs 13, wherein each one of the fastening limbs 13 has a nose-like projection 13a. As shown in FIG. 4, the end regions of the fastening limbs 13 are canted to facilitate the insertion of the limbs of the instrument. The limb of the instrument 7 has a depression 14 and a projection 15 in its proximal end region. The nose-like projection 13a engages with the depression 14 and engages behind the projection 15. The contact point between the nose-like projection 13a and the limb of the instrument 7 forms a first electrical and mechanical contact point. The limb of the instrument 7 further has a planar region 16 in its proximal end region. The planar region 16 of the electrode shaft lies against a planar inner side 17 of the fastening limb 13 of the spring element 5 and forms a second electrical and mechanical contact point. The planar inner side 17 of the fastening limb 13 lies opposite the fastening limb 13 with the nose-like projection 13a.

Figure 5:
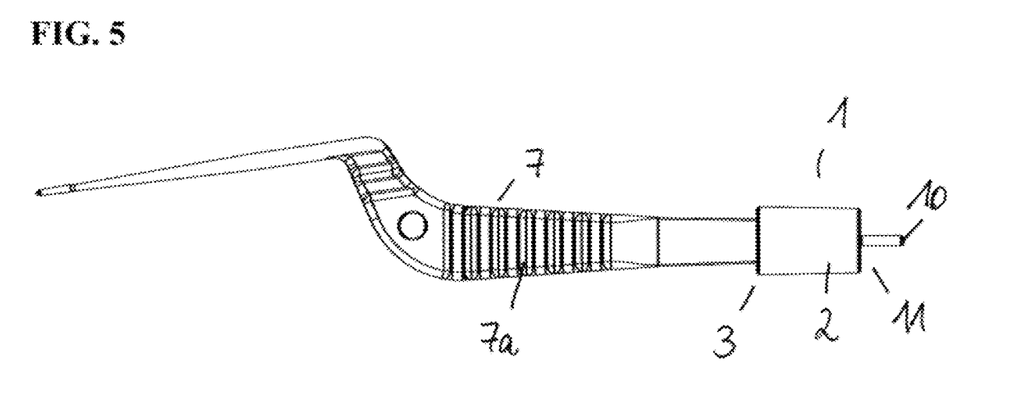
FIG. 5 is a representation of an application example of the plug connector.

FIG. 5 shows a medical instrument according to an embodiment of the invention. In the embodiment shown, the medical instrument is formed by a bipolar forceps, the forceps limbs 7 of which are connected to one another by the connector plug 1. The illustration shows an instrument handle (7a).

Figure 6:
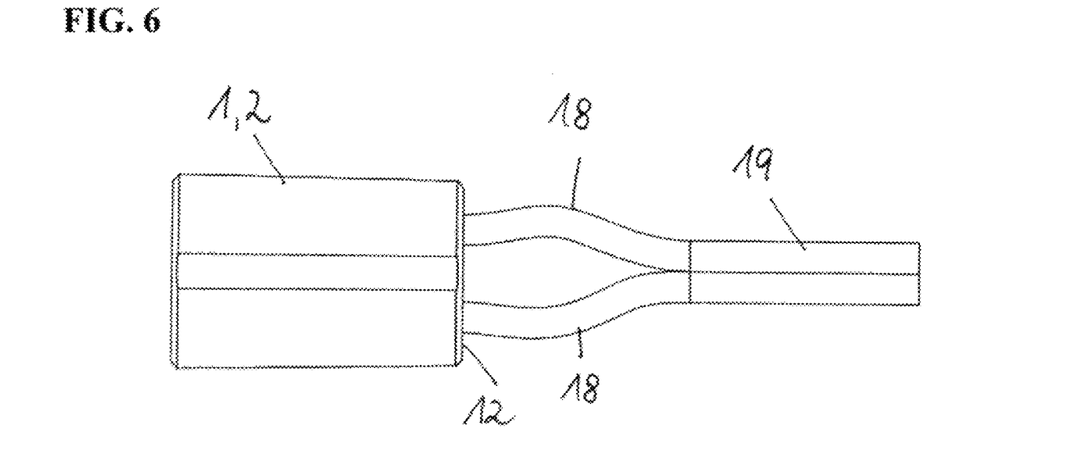
FIG. 6 is a representation of a further exemplary embodiment of the connector plug.

FIG. 6 shows a further embodiment of the connector plug 1. Instead of the contact pins 10, two cables 18 are provided, which are inserted into the passage openings 12 and are conductively connected to the spring elements 5. The cables 18 create a connection to a current source. The cables 18 are combined into a cable harness 19.

Figure 7A:
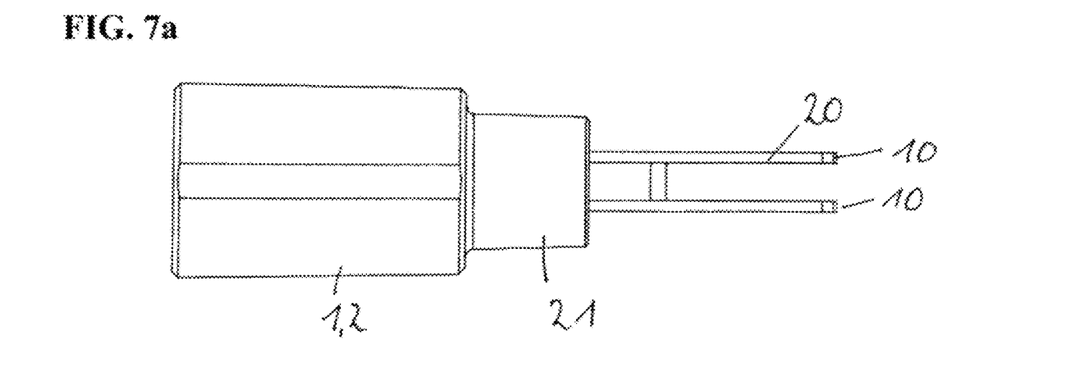
FIGS. 7a and 7b are representations of a further exemplary embodiment of the connector plug as a flat plug.
Figure 7B:
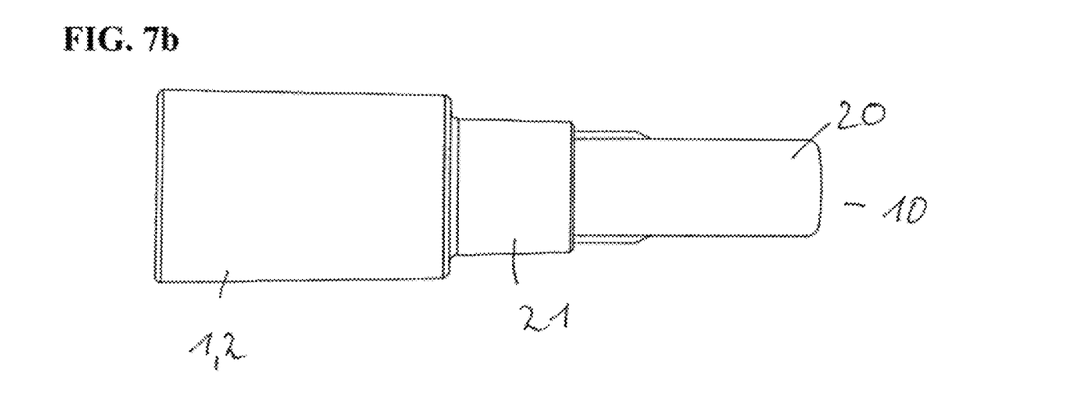

FIGS. 7a and 7b show a further embodiment of the connector plug 1, wherein the contact pins 10 are configured as an elongated, flat metal body. The metal bodies form a flat plug 20 and enable connection to an electrical current source. In the embodiment as a European flat plug 20, the insulating body 2 of the connector plug 1 has a displaced region 21 with a smaller cross-section. The displaced region 21 has a smaller diameter than the rest of the insulating body 2 and is designed in its dimensions to be complementary to a corresponding cable plug.

FIG. 7a shows a top view of the connector plug 1, wherein the two contact pins 10 are shown parallel side by side. The two contact pins 10 are stabilized by an intermediate piece 22.

LIST OF REFERENCE NUMBERS

1 Connector plug
2 Insulating body
3 End face of the insulating body
4 Openings
5 Spring elements
6 Inner walls of the insulating body
7 Limb of an instrument
7a Instrument handle
8 Beveled side walls
9 Channels
10 Contact pins
11 End face of the insulating body
12 Passage openings
13 Fastening limbs
13a Nose-like projection
14 Depression
15 Projection
16 Planar region of the electrode shaft
17 Planar inner side of the spring element
18 Cable
19 Cable harness
20 Flat connector
21 Displaced region
22 Intermediate piece

The invention claimed is:

1. A bipolar electrode or forceps comprising:
two limbs (7) each forming an electrode and terminating at a free proximal end, wherein each of the limbs (7) includes a projection (15) adjacent to the proximal end and a planar region (16) opposite to the projection (15), and
a connector plug (1) having an insulating body (2) for connecting the proximal ends of the limbs (7) of the bipolar electrode or forceps, wherein the insulating body (2) has first and second openings (4) for receiving the proximal ends of the limbs (7) respectively, and, a latching or spring element (5) provided in each of the first and second openings (4) for fastening a corresponding one of the proximal ends of the limbs (7) to the insulating body (2), wherein the first and second openings are bounded by an outer wall and separated by a middle insulated section of the insulating body (2),
wherein each of the latching or spring elements (5) includes electrically conductive material and is formed with a U-shaped cross section with first and second fastening limbs (13) and an open side therebetween, the first fastening limb (13) including a nose-like projection (13a) extending towards the second fastening limb (13), the second fastening limb (13) including a planar inner side (17) facing the first fastening limb (13), wherein the latching or spring elements (5) are provided in the first and second openings (4), respectively, to be located between the outer wall and the middle insulated section with a clearance adjacent to the corresponding first fastening limb (13) and,
wherein, with the proximal ends of the limbs (7) received in the latching or spring elements (5) respectively, for each of the latching or spring elements (5): i. the nose-like projection (13a) engages the corresponding limb (7) adjacent to the projection (15) thereof to form an electrical connection therewith, and ii. the planar inner side (17) engages the planar region (16) of the corresponding limb (17) to form a second electrical connection therewith, wherein the nose-like projection (13a) resists withdrawal of the projection 15 of the corresponding limb (7).

2. The bipolar electrode or forceps according to claim 1, wherein, the proximal ends of the limbs (7), when viewed in cross-section, are each configured to be at least partially complementary to inner sides of the corresponding latching or spring element (5).

3. The bipolar electrode or forceps according to claim 1, wherein, for each of the latching or spring elements (5), the first and second fastening limbs (13) are made of electrically conductive material.

4. The bipolar electrode or forceps according to claim 1, wherein the connector plug (1) further includes two contact pins (10) which penetrate the insulating body (2) on the proximal end face (11) and are electrically connected to the latching or spring elements (5).

5. The bipolar electrode or forceps according to claim 4, wherein the contact pins (10) are formed by metal bodies (20) which are configured plate-shaped or platelet-shaped.

6. The bipolar electrode or forceps according to claim 5, wherein the metal bodies (20) form a flat plug.

7. The bipolar electrode or forceps according to claim 4, wherein the contact pins (10) are welded or soldered to the latching or spring elements (5).

8. The bipolar electrode or forceps according to claim 1, wherein the connector plug (1) further includes two cables (18) with electrical leads contained therein, wherein the cables penetrate the insulating body at the proximal end face, and wherein the electrical leads are electrically connected to the latching or spring elements (5).

9. The bipolar electrode or forceps according to claim 1, wherein each of the proximal ends of the limbs (7) includes a depression (14) adjacent to the projection (15) formed to receive the nose-like projection (13a) of the corresponding latching or spring element.

10. The bipolar electrode or forceps according to claim 1, the insulating body (2) further including a proximal end face (11) extending transversely across, and delimiting, the first and second openings (4).

11. The bipolar electrode or forceps according to claim 1, wherein, for each of the latching or spring elements (5), the first and second fastening limbs (13) run substantially parallel to one another at least in sections.

12. The bipolar electrode or forceps according to claim 1, wherein the insulating body (2) is formed by a plastic sleeve.

13. The bipolar electrode or forceps according to claim 1, wherein the first and second openings (4) each have, when viewed in the cross-section perpendicular to a longitudinal axis of the insulating body (2), two opposing, planar and non-parallel side walls (6), between which the corresponding latching or spring element (5) is located.

14. The bipolar electrode or forceps according to claim 13, wherein the limbs (7) are each formed with beveled side walls (8) to complementarily engage the non-parallel side walls (6) of the first and second openings (4) respectively.

15. The bipolar electrode or forceps according to claim 1, wherein the insulating body (2) has one or more inlet channels (9) for filling the insulating body with a casting compound.

16. The bipolar electrode or forceps according to claim 15, wherein the one or more inlet channels (9) are arranged together with the openings (4) on one end face of the insulating body.

17. The bipolar electrode or forceps according to claim 1, wherein the proximal ends of the limbs (7) are each formed with a greater width than the respective latching or spring element (5) so as to extend laterally therefrom with the proximal ends of the limbs (7) being received in the latching or spring elements (5).

18. The bipolar electrode or forceps according to claim 1, wherein the clearances are each located adjacent to the outer wall.

\* \* \* \* \*